United States Patent [19]

Bonine

[11] Patent Number: 4,562,743

[45] Date of Patent: Jan. 7, 1986

[54] CABLE ELONGATION MEASUREMENT APPARATUS

[75] Inventor: Richard L. Bonine, Portland, Tex.

[73] Assignee: Gearhart Industries, Inc., Fort Worth, Tex.

[21] Appl. No.: 612,325

[22] Filed: May 21, 1984

[51] Int. Cl.$^4$ ............................................. G01N 3/08
[52] U.S. Cl. ........................................ 73/828; 73/158
[58] Field of Search ............ 73/828, 831, 856, 862.39, 73/858, 826, 855, 862.42, 158; 33/147 D, 148 D, 127, 141 R (U.S. only); 254/395–397, 272–273

[56] References Cited

U.S. PATENT DOCUMENTS

| | | | |
|---|---|---|---|
| 1,300,790 | 4/1919 | Tretch | 33/147 D |
| 1,382,663 | 6/1921 | Metzger | 33/147 D |
| 2,017,876 | 10/1935 | Tripolitis | 33/147 D |
| 2,099,662 | 11/1937 | Slonneger | 33/147 D |
| 2,814,883 | 12/1957 | Strimel | 33/147 D |
| 3,921,443 | 11/1975 | Yates | 73/830 |
| 4,211,013 | 7/1980 | Bresson et al. | 33/147 R |
| 4,287,759 | 9/1981 | Cooper | 254/273 |

*Primary Examiner*—Stewart J. Levy
*Assistant Examiner*—Robert R. Raevis
*Attorney, Agent, or Firm*—Hubbard, Thurman, Turner & Tucker

[57] ABSTRACT

A cable elongation or relaxation measurement apparatus comprises an elongated beam having spaced apart clamp assemblies for forcibly clamping a section of cable under tension. One of the clamp assemblies is slidably mounted on a pair of parallel bearing rods secured to the beam and is centered between opposite ends of the rods by coil springs. The movable cable clamp assembly supports a dial indicator which is engageable with an adjustable fixed abutment member supported on the beam so that movement of the movable clamp assembly can be measured for a known change in load on the cable. The support beam includes a pair of spaced apart support roller assemblies each including an upstanding bracket supporting a first roller and a movable support plate supporting a second roller. The second roller may be moved relative to the first roller between a cable engaging and clamping position and a position which permits mounting and demounting the apparatus with respect to the cable.

9 Claims, 7 Drawing Figures

CABLE ELONGATION MEASUREMENT APPARATUS

BACKGROUND OF THE INVENTION

Field of the Invention

The present invention pertains to an apparatus for measuring stretch or elongation in a cable under tension for determining the elongation versus load characteristics of the cable.

BACKGROUND

In the art of gauges for measuring the elongation or compression of various structures several devices have been developed which provide for clamping the structure to be stressed at spaced apart points and measuring the movement of one of the clamps relative to the other to determine the elongation or compression of the test specimen. Prior art measurement devices are not particularly suited for the measurement of elongation of cables under tension so that a relatively accurate stretch versus load factor can be determined.

One application which requires field testing of cables to determine stretch characteristics in the art of well logging tools and similar devices which are lowered on the end of an elongated flexible cable several hundred or several thousand feet into a wellbore. In such applications it is important to know the amount of elongation of the cable so that accurate positioning of the logging device or other apparatus attached to the cable may be determined.

Accordingly, it is particularly important to provide an elongation measurement device which may be easily utilized in a laboratory setting as well as in field use to measure cables which have been placed under a predetermined load or to measure a change in load on a cable having known elongation characteristics. In this regard, the present invention provides an improved elongation measurement apparatus particularly adapted for use in measuring elongation or relaxation of flexible wire cables and the like.

SUMMARY OF THE INVENTION

The present invention provides an improved apparatus for measuring elongation or relaxation of a flexible cable under a tensile load whereby changes in cable length as a result of changing the load a predetermined amount may be measured to determine load/elongation characteristics.

In accordance with one aspect of the present invention there is provided an apparatus for measuring elongation and relaxation of a flexible cable having a pair of clamps mounted spaced apart on an elongated beam and operable to be clamped to a section of cable under tension and wherein one of the clamps is movable relative to the beam for actuation of an indicator device to measure changes in length of the section of cable extending between the clamps. The movable clamp is mounted for sliding movement on a pair of parallel extending bearing rods and includes an arm on which an indicator device is mounted for movement relative to a member mounted stationary on the support beam. The movable clamp is mounted between opposed springs for positioning the clamp on the bearing rods substantially equidistant between limit positions so that cable elongation or relaxation can be measured in accordance with the characteristics of the load change placed on the cable.

In accordance with another aspect of the present invention a cable elongation or relaxation measurement device is provided comprising an elongated beam with spaced apart cable gripping clamps and spaced apart hanger members for supporting the apparatus on the cable during measurement operations. The cable hanger members include opposed roller sets which are movable relative to each other between cable engaging positions and positions for mounting and demounting the measurement apparatus with respect to the cable.

In accordance with still a further aspect of the present invention a cable elongation measurement apparatus is provided which is easily adjusted to calibrate the indicator device and to position the indicator device for ease of viewing during measurement operations. The measurement apparatus is particularly easy to mount on and demount from a cable which is already taut.

The above described features and advantages of the present invention as well as additional superior aspects thereof will be further appreciated by those skilled in the art upon reading the following detailed description in conjunction with the drawing.

DESCRIPTION OF THE PREFERRED EMBODIMENT

Figure 1:
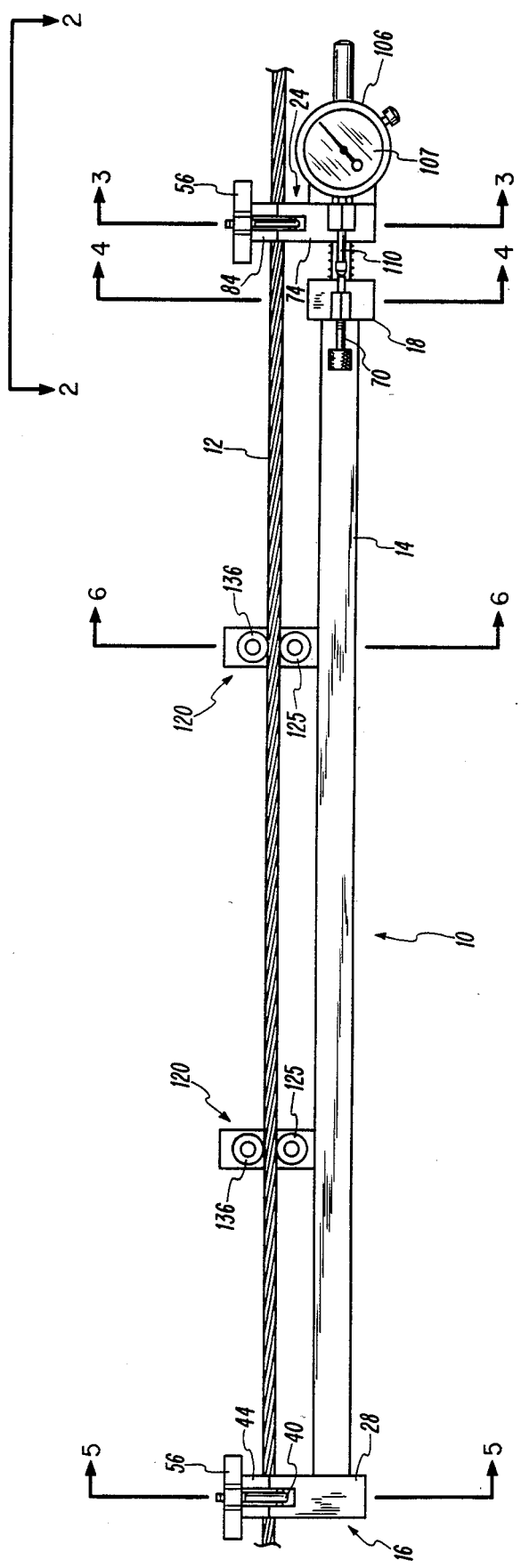
FIG. 1 is a longitudinal side elevation of the cable elongation measurement apparatus of the present invention.

In the description which follows like parts are marked throughout the specification and drawing with the same reference numerals, respectively. The drawing is not necessarily to scale and certain features may be exaggerated in scale in the interest of clarity.

Figure 2:
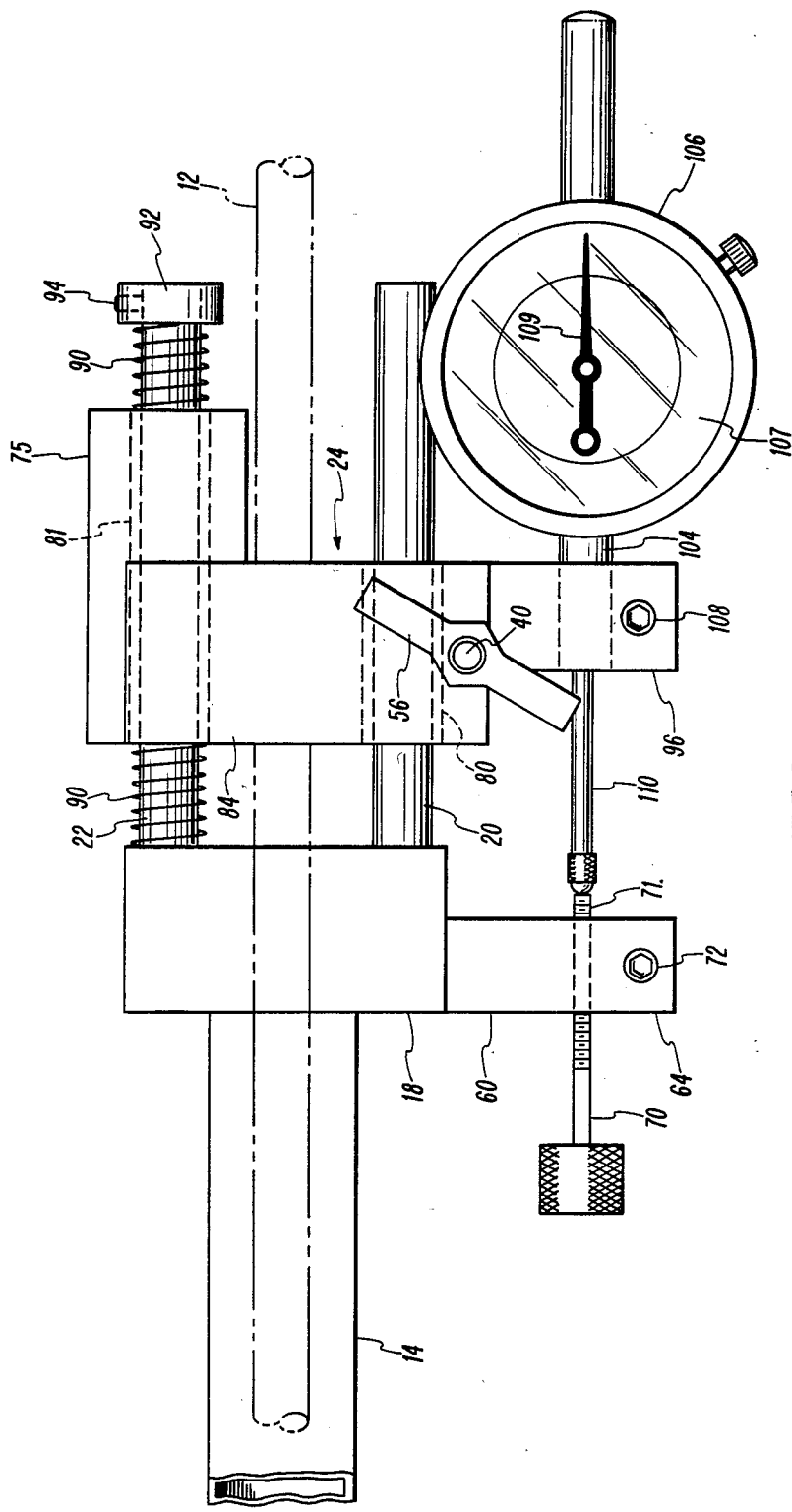
FIG. 2 is a detail plan view taken generally from the line 2—2 of FIG. 1 on a larger scale.

Referring to FIGS. 1 and 2, the cable elongation and relaxation measurement apparatus is illustrated in a typical working position and generally designated by the numeral 10. The apparatus 10 is shown mounted on a section of flexible wire rope or steel cable 12 which is under a predetermined tensile load which may be accomplished by various suitable means, not shown. In the utilization of the apparatus 10, the cable 12 is normally stretched taut under a predetermined load or under a load which may be changed by an amount which can be determined if the load-deflection characteristics of the cable are known.

The apparatus 10 comprises an elongated substantially square cross-section tubular beam 14 which is of sufficient stiffness to resist undergoing perceptible deflection under the changes in load on the cable 12 to be measured by the apparatus 10. The apparatus 10 includes a first cable clamp assembly 16, FIG. 1, fixed to one end of the beam 14 and a support bracket 18 secured to the opposite end of the beam 14 for supporting a pair of elongated cylindrical bearing rods 20 and 22. The bearing rods 20 and 22 are operable to support a clamp assembly 24 slidably mounted on the bearing rods and movable relative to the beam 14, the clamp assembly 16 and the bracket 18.

Figure 5:
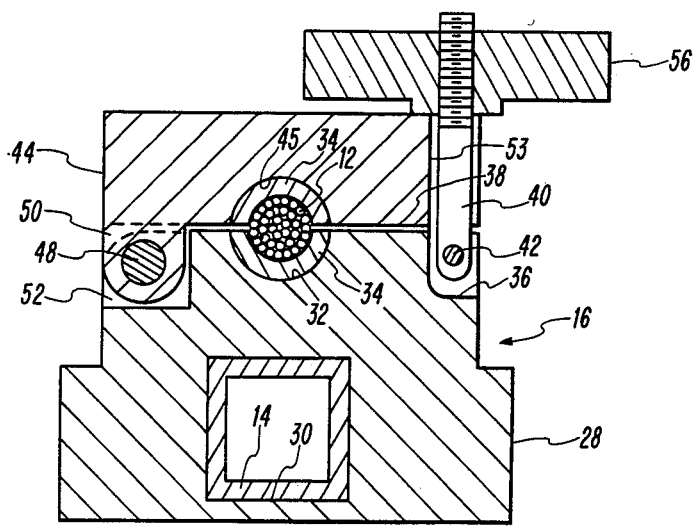
FIG. 5 is a section view taken along the line 5—5 of FIG. 1.

Referring now to FIG. 5, the clamp assembly 16 includes a base member 28 which is provided with an opening 30 for receiving one end of the tubular beam 14 in closefitting relationship to the base member. The beam 14 may be suitably secured to the base member by means such as an interference fit, welding or any suitable substantially permanent method of attachment. The base member 28 includes an arcuate recess 32 for receiving a relatively soft metal annular insert 34 which may be made of copper or a similar metal which will yield under clamping forces when engaging the circumference of the cable 12. The base member 28 is also provided with a recess 36 intersecting a jaw face 38 for receiving a hinged clamping pin 40 which is mounted on a pivot shaft 42 for swinging movement into and out of position in engagement with a clamping jaw 44 pivotally mounted on the base member 28. The clamping jaw 44 is mounted on the base member 28 for pivotal movement between an open cable receiving position and a closed cable clamping position by a hinge pin 48 journalled in respective bosses 50 on the jaw 44 and 52 on the base member 28. The clamping jaw 44 also includes an annular jaw insert 34 suitably secured in a recess 45. The jaw 44 is provided with a slot 53 for receiving the clamping pin 40 which may be swung into and out of position for retaining the clamping jaw 44 forcibly bearing against the cable to clamp the cable between the jaw inserts 34 on the jaw 44 and the base member 28. The pin 40 is threaded at its distal end for receiving a wing nut 56 for securing the clamping jaw 44 in the closed and clamped position.

Figure 4:
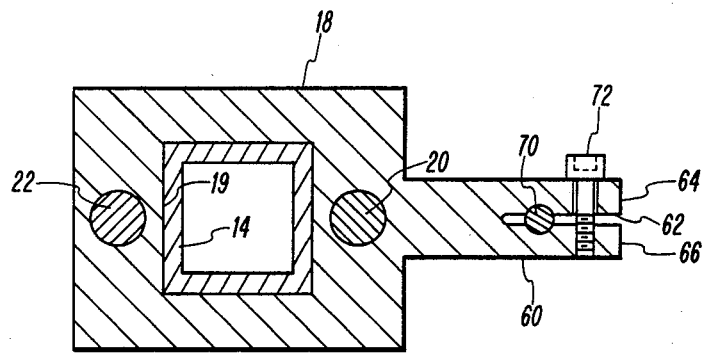
FIG. 4 is a section view taken along the line 4—4 of FIG. 1.

Referring briefly to FIG. 4, the bracket 18 is also provided with a rectangular cross-section opening 19 for receiving the opposite end of the beam 14 which is secured in the opening by suitable means as described earlier with respect to the connection of the base member 28 to the opposite end of the beam. The bracket 18 is adapted to support the coextensive parallel bearing rods 20 and 22 in suitable bores formed in the bracket. The bracket 18 includes an arm 60 extending from one side thereof which is provided with an elongated slot 62 opening to the distal end of the arm to form opposed tines 64 and 66. Internal threads are formed on the tines 64 and 66 for receiving an elongated threaded adjustment rod 70. The rod 70 is operable to be clamped tightly or at least snubbed in a selected position by a socket head screw 72 which extends through a bore in the tine 66 and is threadedly engaged with the tine 64 for drawing the tines toward each other.

Figure 3:
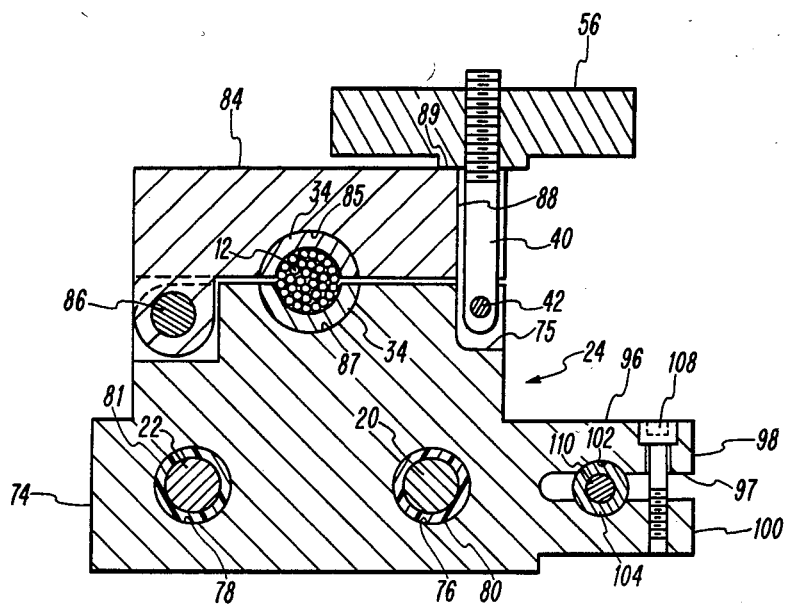
FIG. 3 is a section view taken along the line 3—3 of FIG. 1.

Referring now to FIGS. 2 and 3, the movable clamping jaw assembly 24 includes a base member 74 having a pair of spaced apart bores 76 and 78 in which are supported sleeve bearings 80 and 81 for slidable support of the clamp assembly 24 on the bearing rods 20 and 22. The clamp assembly 24 includes a movable clamping jaw 84 which is pivotally connected to the base member 74 by a hinge pin 86. The clamping jaw 84 and the base member 74 are provided with arcuate recesses 85 and 87, respectively, in which jaw inserts 34 are suitably retained and are forcibly engageable with the cable 12. The jaw 84 is also secured to the base member 74 by a second clamping pin 40 pivotally mounted on the base member 74 in a recess 75 by a second hinge pin 42. The pin 40 is also threadedly engaged with a wing nut 56. The pin 40 is movable from a retracted position clear of the jaw 84 into a recess 88 so that the nut 56 may be engaged with jaw surface 89 to secure the jaw in the cable clamped position. The jaw inserts 34 on both clamp assemblies 16 and 24 are suitably aligned with respect to the central axes of the bearing rods 20 and 22 such that the central axis of the cable 12 is equidistant from the central axes of the respective bearing rods to provide more uniform loading on the bearings 80 and 81.

The base member 74 includes an integral axially extending portion 75 forming an extended bore for the bearing insert 81. Opposed coil springs 90 are sleeved over the bearing rod 22 and are interposed between the base member 74 and the bracket 18, and between the integral extension 75 and the distal end of the rod 22, respectively. A removable collar 92 is disposed on the distal end of the bearing rod 22 for retaining the spring 90 on the rod as indicated in FIG. 2. A set screw 94 is provided for retaining the collar 92 on the bearing rod. The springs 90 are provided with equal force-deflection characteristics to substantially center the clamp assembly 24 between the opposing faces of the bracket 18 and the collar 92.

The base member 74 also includes a laterally extending bifurcated arm 96, FIG. 3, having a slot 97 opening to the distal end of the arm and forming opposed tines 98 and 100. A partial cylindrical bore 102 is formed in and between the tines 98 and 100 for receiving a tubular support shank 104 of a dial indicator 106. A socket head screw 108 extends between the tines 98 and 100 and is threadedly engaged with the tine 100 for clamping the support shank 104 of the indicator 106 in a selected rotative position of the indicator face 107 with respect to the clamp assembly 24. The dial indicator 106 may be one of several types commercially available and, for example, may be a type manufactured by L. S. Starrett Company, Athol, Mass. as their part number 25-881. The dial indicator 106 includes an actuating stem 110 which extends through the tubular shank 104 and is adapted to engage the distal end 71 of the adjusting screw 70, FIG. 2, mounted on the bracket arm 60.

Figure 6:
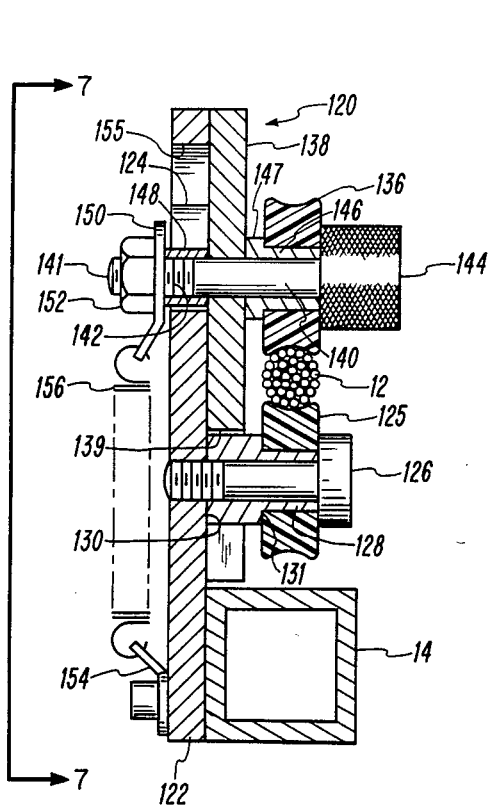
FIG. 6 is a section view taken along the line 6—6 of FIG. 1.
Figure 7:
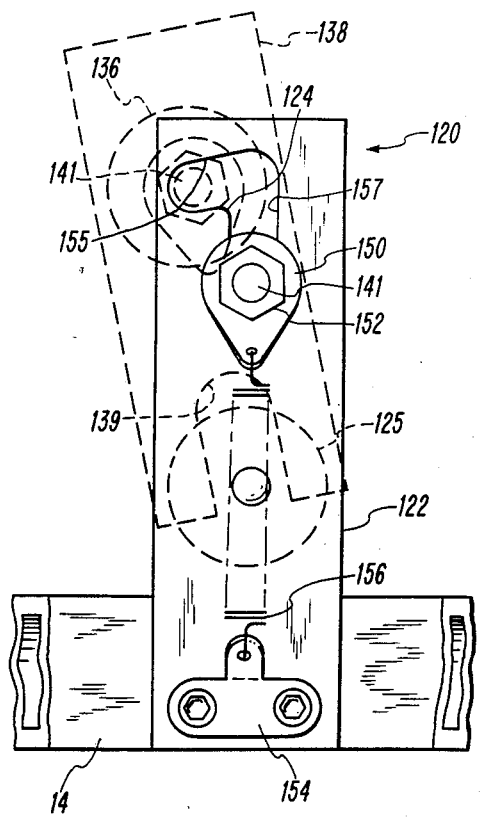
FIG. 7 is a view taken from the line 7—7 of FIG. 6.

Referring now to FIGS. 1, 6 and 7, the apparatus 10 includes means for supporting the apparatus on the cable 12 to facilitate the use of the apparatus when setting up for measurement of elongation or relaxation of a section of cable. A pair of spaced apart releasable support roller assemblies are supported on the beam 14 and are each generally designated by the numeral 120. The support roller assemblies 120 are of identical construction and, as indicated in FIGS. 6 and 7, are characterized by a support plate 122 secured to the beam 14. The support plate 122 includes a somewhat inverted J shaped slot 124 formed therein, as indicated in FIGS. 6 and 7, for a purpose to be described hereinbelow. The support roller assemblies 120 each include a first support roller 125 rotatably supported on the plate 122 by a shaft formed by a socket head screw 126 which is threadedly engaged with the plate 122 and supports a suitable bearing bushing 128 between the screw head 129 and the face 130 of the plate 122. The bushing 128 includes a transverse shoulder 131 for maintaining the position of the roller 125 spaced from the plate face 130. The bearing bushing 128 is dimensioned such with respect to the width of the roller 125 such that, when assembled on the plate 122 as shown, the roller is free to rotate. The bearing bushing 128 may be made of a suitable bearing material requiring infrequent or no external lubrication.

A second support roller 136 is also provided on the support roller assembly 120 and is mounted for rotation on a support plate 138 by a shaft 140 having a threaded end 142 and a head 144 comprising a knob for grasping the shaft. A bearing bushing 146 is interposed between the roller 136 and the shaft 140 for rotatably supporting the roller 136 on the shaft. The bushing 146 includes a transverse shoulder 147 for locating the roller 136 spaced from the plate 138. A slot 139 is formed in the plate 138 to provide clearance around the bushing portion forming the shoulder 131. The shaft 140 extends into and through the J slot 124 and is provided with spacer 148 between the end 141 of the shaft and the plate 138. A spring retention bracket 150 is secured on the shaft by a nut 152. A second spring retention bracket 154 is secured to the plate 122 and a coil spring 156 is connected to the brackets 150 and 154 for biasing the roller 136 toward the roller 125 to forcibly engage the cable 12 as shown by the position of the rollers 136 in FIGS. 1 and 6. The roller 136 may be moved away from the roller 125 to permit insertion of and removal of the cable 12 between the rollers by moving the shaft 140 upward, viewing FIGS. 6 and 7, and into the branch arm 155 of the J slot as indicated by the alternate position of the roller 136 and the plate 138 in FIG. 7.

Accordingly, when the roller support shafts 140 are moved into the branch arms 155 of the J slots sufficient clearance is provided between the rollers 125 and 136 to permit hanging the apparatus 10 on a stretched cable, and removing the apparatus from the cable if the clamp assemblies 16 and 24 are in an open position to permit removal of the cable from between the jaws of the respective clamp assemblies. When it is desired to steady the apparatus 10 on a taut cable preparatory to engaging the clamp assemblies 16 and 24, the knobs 144 are grasped to move the shafts 140 into the main arm 157 of the J slot, FIG. 7, whereby the springs 156 are operable to forcibly move the plates 138 to snugly engage the cable 12 between the rollers 136 and 125 and to retain the apparatus 10 on the cable 12 while the jaw 44 is swung into the closed position and clamped by the pin 40 and wing nut 56. The clamp assembly 24 is then closed prior to setting the dial indicator 106 for measurement of elongation or relaxation of the cable 12. When it is desired to remove the apparatus 10 from the cable 12, the clamp assemblies 16 and 24 are released and the support roller assemblies 120 are actuated to move their respective roller 136 to the alternate position indicated in FIG. 7 so that the apparatus 10 may be removed from the cable 12.

The radius centers of the bores formed by the inserts 34 of the jaw assemblies 16 and 24, for a selected cable size, are coincident with an axis which extends between the jaw assemblies 16 and 24 and lies in a plane passing through the center of the rollers 136 and 125 and perpendicular to the respective axes of rotation of the rollers so that, in the closed condition of the roller assemblies 120 and the clamp assemblies 16 and 24, there is no lateral load imposed on the cable or on the apparatus 10.

The cable elongation measuring apparatus 10 is typically placed in operation on a cable which is under a known tension by opening the jaws 44 and 84 and the roller assemblies 120 and suspending the apparatus on the taut cable by engaging the rollers 136 with the upper surface of the cable. Both the rollers 125 and 136 are suitably grooved to provide for retaining the rollers engaged with the cable 12 and centering the rollers with respect to the cable. The roller assemblies 120 are then moved to the cable clamping position previously described to firmly support the apparatus 10 on the cable 12. However, the rollers 125 and 136 are freely rotatable so that they do not influence the reading of the elongation of relaxation of the cable during the measurement process. Clamping jaw 44 is then closed and its associated locking pin 40 swung into position and wing nut 56 manually tightened against the jaw to firmly grip the cable 12 with the clamp assembly 16. The face 107 of dial indicator 106 may be oriented in a selected convenient viewing position by loosening screw 108 sufficiently to rotate the indicator to one of the positions shown in FIGS. 1 or 2, for example, and the screw then retightened.

The clamp assembly 24 is then inspected to determine that the base member 74 is substantially centered between the springs 90 and freely movable and that the adjusting screw 70 is retracted out of engagement with the indicator stem 110. The clamping jaw 84 is then closed and locked by its associated pin 40 and wing nut 56. At this point the cable tension may be fine adjusted to the precise amount or starting point desired. When the exact starting tension is obtained the adjusting screw 70 is brought into engagement with the indicator stem 110 just sufficiently that perceptible movement of the indicator needle 109 or other readout device is indicated. The indicator 106 is then read or preset in a conventional manner. After the zero or preset reading of the indicator 106 is obtained the tension in the cable 12 is increased or decreased as desired by a predetermined amount and the change in the reading of the dial indicator 106 is noted. Thanks to the arrangement of the clamp assembly 24 on its support rods 20 and 22 the clamp assembly may move in either direction relative to the clamp assembly 16 so that a change in cable elongation or relaxation for a predetermined change in load on the cable may be measured. Conversely, if the load/deflection characteristics of the cable are known, a measured elongation or contraction of the cable may be measured to determine the change in load on the cable.

Although a preferred embodiment of the invention has been described in detail herein those skilled in the art will recognize that various substitutions and modifications may be made to the structure without departing from the scope and spirit of the invention as recited in the appended claims.

What I claim is:

1. Apparatus for measuring a change in the elongation of a flexible cable or the like as a result of changing a tensile load on said cable, comprising:

an elongated beam including a first clamp assembly disposed at one end of said beam for releasably clamping said apparatus to said cable;

a second clamp assembly supported on said beam and movable relative to said beam and said first clamp assembly;

indicator means for measuring the distance of movement of said second clamp assembly relative to said beam; and means for supporting said apparatus on said cable independent of said clamp assemblies and permitting linear transversal of said cable relative to said beam between said clamp assemblies when said clamp assemblies are engaged with and released from said cable, said means for supporting said apparatus including at least first and second rollers supporting on and spaced apart along said beam for supporting said apparatus on said cable, said first roller being disposed on a first member connected to said beam and supporting a third roller for rotation relative to said first member, one of said first and third rollers being mounted on a support plate movable relative to said first member, and said first and third rollers being yieldably biased toward each other to engage said cable between said first and third rollers for supporting said apparatus on said cable.

2. The apparatus set forth in claim 1 wherein:
said second roller is disposed on a second member connected to said beam at a point spaced substantially from said first member, said second member supports a fourth roller for rotation relative to said second member, one of said second and fourth rollers being mounted on a support plate movable relative to said second member, and said second and fourth rollers are yieldably biased toward each other to engage said cable between said second and fourth rollers for supporting said apparatus on said cable.

3. The apparatus set forth in claim 2 including:
means for holding said first and second rollers spaced apart from said third and fourth rollers, respectively, said means including a support shaft on respective ones of said plates and disposed in a J slot in said first and second members, respectively, for holding said plates in a position of said first and second rollers to permit mounting said apparatus on and removing said apparatus from said cable.

4. The apparatus set forth in claim 1 including:
bearing means for supporting said second clamp assembly for movement relative to said beam, and means for yieldably biasing said second clamp assembly in a substantially centered position along said bearing means whereby said second clamp assembly is movable in opposite directions relative to said beam in response to a change in the elongation of said cable.

5. The apparatus set forth in claim 4 wherein:
said bearing means comprises at least two spaced apart and parallel bearing rods for supporting said clamp assembly for slidable movement along said bearing rods.

6. The apparatus set forth in claim 5 wherein:
said biasing means includes opposed springs acting on said second clamp assembly.

7. The apparatus set forth in claim 4 including:
an adjustment member supported by said beam and movable into engagement with said indicator means when said second clamp assembly is clamped to said cable and in a balanced position of said second clamp assembly.

8. The apparatus set forth in claim 7 including:
means for snubbing said adjustment member to secure said adjustment member in a selected position relative to said beam.

9. The apparatus set forth in claim 1 including:
means for supporting said indicator means in a selected one of plural positions on said second clamp assembly.

* * * * *